(12) United States Patent
Ward et al.

(10) Patent No.: US 9,149,235 B2
(45) Date of Patent: Oct. 6, 2015

(54) OEDEMA DETECTION

(71) Applicant: Impedimed Limited, Pinkenba, Queensland (AU)

(72) Inventors: Leigh Ward, Kenmore Hills (AU); Brian Cornish, Brisbane (AU)

(73) Assignee: Impedimed Limited, Pinkenba, Queensland (AU)

( * ) Notice: Subject to any disclaimer, the term of this patent is extended or adjusted under 35 U.S.C. 154(b) by 0 days.

(21) Appl. No.: 14/136,463

(22) Filed: Dec. 20, 2013

(65) Prior Publication Data

US 2014/0107522 A1    Apr. 17, 2014

Related U.S. Application Data

(63) Continuation of application No. 11/629,832, filed as application No. PCT/AU2005/000876 on Jun. 17, 2005.

(30) Foreign Application Priority Data

Jun. 18, 2004  (AU) ................................ 2004903314

(51) Int. Cl.
*A61B 5/00* (2006.01)
*A61B 5/053* (2006.01)

(52) U.S. Cl.
CPC ............. *A61B 5/7225* (2013.01); *A61B 5/0537* (2013.01); *A61B 5/4869* (2013.01); *A61B 5/4878* (2013.01)

(58) Field of Classification Search
CPC .. A61B 5/0537; A61B 5/4878; A61B 5/4869; A61B 5/053; A61B 5/0531; A61B 5/4875

USPC ......................................................... 600/547
See application file for complete search history.

(56) References Cited

U.S. PATENT DOCUMENTS

| 3,316,896 A | 5/1967 | Thomasset |
| 3,851,641 A | 12/1974 | Toole et al. |
| 3,868,165 A | 2/1975 | Gonser |

(Continued)

FOREIGN PATENT DOCUMENTS

| CA | 2231038 | 11/1999 |
| CA | 2638958 | 6/2000 |

(Continued)

OTHER PUBLICATIONS

European Search Report dated Jun. 27, 2005 and Written Opinion dated Jul. 6, 2005 for PCT/AU2005/000876 filed Jun. 17, 2005.

(Continued)

*Primary Examiner* — Max Hindenburg
(74) *Attorney, Agent, or Firm* — Knobbe Martens Olson & Bear LLP (57) ABSTRACT

A method of detecting tissue oedema in a subject. The method includes determining a measured impedance for first and second body segments. An index indicative of a ratio of the extra-cellular to intra-cellular fluid is then calculated for each body segment, with these being used to determine an index ratio based on the index for the first and second body segments. The index ration can in turn be used to determine the presence, absence or degree of tissue oedema, for example by comparing the index ratio to a reference or previously determined index ratios.

52 Claims, 4 Drawing Sheets

(56) References Cited

U.S. PATENT DOCUMENTS

| | | |
|---|---|---|
| 3,871,359 A | 3/1975 | Pacela |
| 4,008,712 A | 2/1977 | Nyboer |
| 4,034,854 A | 7/1977 | Bevilacqua |
| 4,121,575 A | 10/1978 | Mills et al. |
| 4,144,878 A | 3/1979 | Wheeler |
| 4,184,486 A | 1/1980 | Papa |
| 4,233,987 A | 11/1980 | Feingold |
| 4,291,708 A | 9/1981 | Frei et al. |
| 4,314,563 A | 2/1982 | Wheeler |
| 4,353,372 A | 10/1982 | Ayer |
| 4,365,634 A | 12/1982 | Bare et al. |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,468,832 A | 9/1984 | Bai et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,832,608 A | 5/1989 | Kroll |
| 4,895,163 A | 1/1990 | Libke et al. |
| 4,899,758 A | 2/1990 | Finkelstein et al. |
| 4,905,705 A | 3/1990 | Kizakevich et al. |
| 4,911,175 A | 3/1990 | Shizgal |
| 4,922,911 A | 5/1990 | Wada et al. |
| 4,942,880 A | 7/1990 | Slovák |
| 4,951,682 A | 8/1990 | Petre |
| 4,981,141 A | 1/1991 | Segalowitz |
| 5,025,784 A | 6/1991 | Shao et al. |
| 5,063,937 A | 11/1991 | Ezenwa et al. |
| 5,078,134 A | 1/1992 | Heilman et al. |
| 5,086,781 A | 2/1992 | Bookspan |
| 5,143,079 A | 9/1992 | Frei et al. |
| 5,197,479 A | 3/1993 | Hubelbank et al. |
| 5,199,432 A | 4/1993 | Quedens et al. |
| 5,246,008 A | 9/1993 | Meuller |
| 5,280,429 A | 1/1994 | Withers |
| 5,305,192 A | 4/1994 | Bonte et al. |
| 5,309,917 A | 5/1994 | Wang et al. |
| 5,311,878 A | 5/1994 | Brown et al. |
| 5,372,141 A | 12/1994 | Gallup et al. |
| 5,415,164 A | 5/1995 | Faupel |
| 5,449,000 A | 9/1995 | Libke et al. |
| 5,465,730 A | 11/1995 | Zadehoochak et al. |
| 5,469,859 A | 11/1995 | Tsoglin et al. |
| 5,503,157 A | 4/1996 | Sramek |
| 5,505,209 A | 4/1996 | Reining |
| 5,511,553 A | 4/1996 | Segalowitz |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,588,429 A | 12/1996 | Isaacson et al. |
| 5,704,355 A | 1/1998 | Bridges |
| 5,730,136 A | 3/1998 | Laufer et al. |
| 5,732,710 A | 3/1998 | Rabinovich et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,919,142 A | 7/1999 | Boone et al. |
| 5,994,956 A | 11/1999 | Concorso |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,101,413 A | 8/2000 | Olson et al. |
| 6,122,544 A | 9/2000 | Organ |
| 6,125,297 A | 9/2000 | Siconolfi |
| 6,142,949 A | 11/2000 | Ubby |
| 6,151,523 A | 11/2000 | Ferrer et al. |
| 6,173,003 B1 | 1/2001 | Whikehart et al. |
| 6,228,022 B1 | 5/2001 | Friesem et al. |
| 6,228,033 B1 | 5/2001 | Koobi et al. |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,496,725 B2 | 12/2002 | Kamada et al. |
| 6,497,659 B1 | 12/2002 | Rafert |
| 6,532,384 B1 | 3/2003 | Fukuda |
| 6,560,480 B1 | 5/2003 | Nachaliel et al. |
| 6,569,160 B1 | 5/2003 | Goldin et al. |
| 6,584,348 B2 | 6/2003 | Glukhovsky |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtk |
| 6,633,777 B2 | 10/2003 | Szopinski |
| 6,643,543 B2 * | 11/2003 | Takehara et al. ............... 600/547 |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,760,617 B2 * | 7/2004 | Ward et al. .................... 600/547 |
| 6,768,921 B2 | 7/2004 | Organ et al. |
| 6,845,264 B1 | 1/2005 | Skladnev et al. |
| 6,870,109 B1 | 3/2005 | Villarreal |
| 6,875,176 B2 | 4/2005 | Mourad et al. |
| 6,906,533 B1 | 6/2005 | Yoshida |
| 6,922,586 B2 | 7/2005 | Davies |
| 6,980,853 B2 | 12/2005 | Miyoshi et al. |
| 7,130,680 B2 | 10/2006 | Kodama et al. |
| 7,132,611 B2 | 11/2006 | Gregaard et al. |
| 7,148,701 B2 | 12/2006 | Park et al. |
| 7,206,630 B1 | 4/2007 | Tarler |
| 7,212,852 B2 | 5/2007 | Smith et al. |
| 7,457,660 B2 | 11/2008 | Smith et al. |
| 7,477,937 B2 | 1/2009 | Iijima et al. |
| 7,499,745 B2 | 3/2009 | Littrup et al. |
| 7,628,761 B2 | 12/2009 | Gozani et al. |
| 7,657,292 B2 | 2/2010 | Baker et al. |
| 7,706,872 B2 | 4/2010 | Min et al. |
| 7,733,224 B2 | 6/2010 | Tran |
| 7,749,013 B2 | 7/2010 | Sato et al. |
| 7,860,557 B2 | 12/2010 | Istvan et al. |
| 8,233,617 B2 * | 7/2012 | Johnson et al. ................. 380/28 |
| 8,233,974 B2 | 7/2012 | Ward et al. |
| 8,467,865 B2 | 6/2013 | Gregory et al. |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0021799 A1 | 9/2001 | Ohlsson |
| 2001/0025139 A1 | 9/2001 | Pearlman |
| 2002/0020138 A1 | 2/2002 | Walker et al. |
| 2002/0022787 A1 | 2/2002 | Takehara et al. |
| 2002/0035334 A1 | 3/2002 | Meij et al. |
| 2002/0072686 A1 | 6/2002 | Hoey et al. |
| 2002/0079910 A1 | 6/2002 | Fukuda |
| 2002/0093992 A1 | 7/2002 | Plangger |
| 2002/0109621 A1 | 8/2002 | Khair et al. |
| 2002/0123694 A1 | 9/2002 | Organ et al. |
| 2002/0161311 A1 | 10/2002 | Ward et al. |
| 2002/0193689 A1 | 12/2002 | Bernstein et al. |
| 2002/0194419 A1 | 12/2002 | Rajput et al. |
| 2003/0004403 A1 | 1/2003 | Drinan et al. |
| 2003/0023184 A1 | 1/2003 | Pitts-Crick et al. |
| 2003/0028221 A1 | 2/2003 | Zhu et al. |

(56) References Cited

U.S. PATENT DOCUMENTS

| | | |
|---|---|---|
| 2003/0036713 A1 | 2/2003 | Bouton et al. |
| 2003/0050570 A1 | 3/2003 | Kodama et al. |
| 2003/0073916 A1 | 4/2003 | Yonce |
| 2003/0105411 A1 | 6/2003 | Smallwood et al. |
| 2003/0120170 A1 | 6/2003 | Zhu et al. |
| 2004/0015095 A1 | 1/2004 | Li et al. |
| 2004/0019292 A1 | 1/2004 | Drinan et al. |
| 2004/0059220 A1 | 3/2004 | Mourad et al. |
| 2004/0059242 A1 | 3/2004 | Masuo et al. |
| 2004/0077944 A1 | 4/2004 | Steinberg et al. |
| 2004/0127793 A1 | 7/2004 | Mendlein et al. |
| 2004/0158167 A1 | 8/2004 | Smith et al. |
| 2004/0167423 A1 | 8/2004 | Pillon et al. |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0236202 A1 | 11/2004 | Burton |
| 2004/0242987 A1 | 12/2004 | Liew et al. |
| 2004/0252870 A1 | 12/2004 | Reeves et al. |
| 2004/0253652 A1 | 12/2004 | Davies |
| 2004/0267344 A1 | 12/2004 | Stett et al. |
| 2005/0033281 A1 | 2/2005 | Bowman et al. |
| 2005/0039763 A1 | 2/2005 | Kraemer et al. |
| 2005/0049474 A1 | 3/2005 | Kellogg et al. |
| 2005/0098343 A1 | 5/2005 | Fukuda |
| 2005/0101875 A1 | 5/2005 | Semler et al. |
| 2005/0107719 A1 | 5/2005 | Arad et al. |
| 2005/0113704 A1 | 5/2005 | Lawson et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2005/0203435 A1 | 9/2005 | Nakada |
| 2005/0261743 A1 | 11/2005 | Kroll |
| 2006/0004300 A1 | 1/2006 | Kennedy |
| 2006/0047189 A1 | 3/2006 | Takehara |
| 2006/0070623 A1 | 4/2006 | Wilkinson et al. |
| 2006/0085048 A1 | 4/2006 | Cory et al. |
| 2006/0085049 A1 | 4/2006 | Cory et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0197509 A1 | 9/2006 | Kanamori et al. |
| 2006/0224079 A1 | 10/2006 | Washchuck |
| 2006/0224080 A1 | 10/2006 | Oku et al. |
| 2006/0252670 A1 | 11/2006 | Fiorucci et al. |
| 2006/0253016 A1 | 11/2006 | Baker et al. |
| 2006/0264775 A1 | 11/2006 | Mills et al. |
| 2006/0270942 A1 | 11/2006 | McAdams |
| 2007/0027402 A1 | 2/2007 | Levin et al. |
| 2007/0043303 A1 | 2/2007 | Osypka et al. |
| 2007/0087703 A1 | 4/2007 | Li et al. |
| 2007/0088227 A1 | 4/2007 | Nishimura |
| 2007/0106342 A1 | 5/2007 | Schumann |
| 2007/0118027 A1 | 5/2007 | Baker et al. |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0039700 A1 | 2/2008 | Drinan et al. |
| 2008/0048786 A1 | 2/2008 | Feldkamp et al. |
| 2008/0091114 A1 | 4/2008 | Min et al. |
| 2008/0183098 A1 | 7/2008 | Denison et al. |
| 2008/0188757 A1 | 8/2008 | Rovira et al. |
| 2008/0205717 A1 | 8/2008 | Reeves et al. |
| 2008/0221411 A1 | 9/2008 | Hausmann et al. |
| 2008/0319336 A1 | 12/2008 | Ward et al. |
| 2009/0043222 A1 | 2/2009 | Chetham |
| 2009/0054952 A1 | 2/2009 | Glukhovsky et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0082679 A1 | 3/2009 | Chetham |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0209828 A1 | 8/2009 | Musin |
| 2009/0264776 A1 | 10/2009 | Vardy |
| 2009/0287102 A1 | 11/2009 | Ward |
| 2009/0318778 A1 | 12/2009 | Dacso et al. |
| 2010/0100146 A1 | 4/2010 | Blomqvist |
| 2010/0168530 A1 | 7/2010 | Chetham et al. |
| 2011/0054343 A1 | 3/2011 | Chetham et al. |
| 2011/0060239 A1 | 3/2011 | Gaw |
| 2011/0087129 A1 | 4/2011 | Chetham et al. |
| 2011/0118619 A1 | 5/2011 | Burton et al. |
| 2011/0190655 A1 | 8/2011 | Moissl et al. |
| 2011/0251513 A1 | 10/2011 | Chetham et al. |

FOREIGN PATENT DOCUMENTS

| | | |
|---|---|---|
| CA | 2613524 | 1/2007 |
| CA | 2615845 | 1/2007 |
| DE | 2912349 | 10/1980 |
| EP | 0249823 | 12/1987 |
| EP | 349043 | 3/1990 |
| EP | 0357309 | 3/1990 |
| EP | 377887 | 7/1990 |
| EP | 339471 | 3/1997 |
| EP | 865763 | 9/1998 |
| EP | 0869360 | 10/1998 |
| EP | 1080686 | 3/2001 |
| EP | 1112715 | 4/2001 |
| EP | 1146344 | 10/2001 |
| EP | 1114610 | 11/2001 |
| EP | 1177760 | 2/2002 |
| EP | 1219937 | 7/2002 |
| EP | 1238630 | 9/2002 |
| EP | 1338246 | 8/2003 |
| EP | 1452131 | 9/2004 |
| EP | 1553871 | 7/2005 |
| EP | 1629772 | 3/2006 |
| EP | 1247487 | 1/2008 |
| EP | 1903938 | 4/2008 |
| EP | 1909642 | 4/2008 |
| EP | 1948017 | 7/2008 |
| FR | 2486386 | 1/1982 |
| FR | 2748928 | 11/1997 |
| GB | 1441622 | 7/1976 |
| GB | 2131558 | 6/1984 |
| GB | 2260416 | 4/1993 |
| GB | 2426824 | 12/2006 |
| JP | 6-74103 | 10/1994 |
| JP | 8191808 | 7/1996 |
| JP | 09051884 | 2/1997 |
| JP | 9220209 | 8/1997 |
| JP | 10000185 | 1/1998 |
| JP | 10014898 | 1/1998 |
| JP | 10014899 | 2/1998 |
| JP | 10-225521 | 8/1998 |
| JP | 11070090 | 3/1999 |
| JP | 2000107138 | 4/2000 |
| JP | 2000139867 | 5/2000 |
| JP | 2001-204707 | 7/2001 |
| JP | 2001-224568 | 8/2001 |
| JP | 2001-245866 | 9/2001 |
| JP | 2001321352 | 11/2001 |
| JP | 2002330938 | 11/2002 |
| JP | 2003-116803 | 4/2003 |
| JP | 2003116805 | 4/2003 |
| JP | 2003-230547 | 8/2003 |
| JP | 2004-61251 | 2/2004 |
| JP | 2008022995 | 7/2008 |
| RU | 2112416 | 6/1998 |
| WO | WO 88/07392 | 10/1988 |
| WO | WO 93-18821 | 9/1993 |
| WO | WO 94-01040 | 1/1994 |
| WO | WO 96-01586 | 1/1996 |
| WO | WO 96/12439 | 5/1996 |
| WO | WO 96/32652 | 10/1996 |
| WO | WO 97/11638 | 4/1997 |

(56) References Cited

FOREIGN PATENT DOCUMENTS

| WO | WO 97-14358 | 4/1997 |
|---|---|---|
| WO | WO 98-06328 | 2/1998 |
| WO | WO 98-12983 | 4/1998 |
| WO | WO 98/23204 | 6/1998 |
| WO | WO 98/33553 | 8/1998 |
| WO | WO 00/40955 | 7/2000 |
| WO | WO 00/79255 | 12/2000 |
| WO | WO 01/50954 | 7/2001 |
| WO | WO 01/67098 | 9/2001 |
| WO | WO 02/053028 | 7/2002 |
| WO | WO 02/062214 | 8/2002 |
| WO | WO 02/094096 | 11/2002 |
| WO | WO 04/000115 | 12/2003 |
| WO | WO 2004-002301 | 1/2004 |
| WO | WO 2004-006660 | 1/2004 |
| WO | WO 2004/026136 | 4/2004 |
| WO | WO 2004/032738 | 4/2004 |
| WO | WO 2004/043252 | 5/2004 |
| WO | WO 2004/047635 | 6/2004 |
| WO | WO 2004/047636 | 6/2004 |
| WO | WO 2004/047638 | 6/2004 |
| WO | WO 2004/049936 | 6/2004 |
| WO | WO 2004/083804 | 9/2004 |
| WO | WO 2004-098389 | 11/2004 |
| WO | WO 2004-112563 | 12/2004 |
| WO | WO 2005/010640 | 2/2005 |
| WO | WO 2005/018432 | 3/2005 |
| WO | WO 2005/027717 | 3/2005 |
| WO | WO 2005/051194 | 6/2005 |
| WO | WO 2005-122888 | 12/2005 |
| WO | WO 2006-129108 | 12/2006 |
| WO | WO 2006-129116 | 12/2006 |
| WO | WO 2007-002991 | 1/2007 |
| WO | WO 2007-002992 | 1/2007 |
| WO | WO 2007-002993 | 1/2007 |
| WO | WO 2007-009183 | 1/2007 |
| WO | WO 2007-041783 | 4/2007 |
| WO | WO 2007-045006 | 4/2007 |
| WO | WO 2007/056493 | 5/2007 |
| WO | WO 2007-105996 | 9/2007 |
| WO | WO 2008-054426 | 8/2008 |
| WO | WO 2008-119166 | 10/2008 |
| WO | WO 2008-138062 | 11/2008 |
| WO | WO 2008-149125 | 12/2008 |
| WO | WO 2009-036369 | 3/2009 |
| WO | WO 2009-100491 | 8/2009 |
| WO | WO 2011-022068 | 2/2011 |
| WO | WO 2011-050393 | 5/2011 |
| WO | WO 2011-075769 | 6/2011 |

OTHER PUBLICATIONS

Abdullah M. Z.; Simulation of an inverse problem in electrical impedance tomography using resistance electrical network analogues; International Journal of Electrical Engineering Education; vol. 36, No. 4, pp. 311-324; Oct. 1999.

Al-Hatib, F.; Patient Instrument connection errors in bioelectrical impedance measurement; Physiological Measurement; vol. 19, No. 2, pp. 285-296; May 2, 1998.

Boulier, A. et al.; Fat-Free Mass Estimation by Two Electrode Impedance Method; American Journal of Clinical Nutrition; vol. 52, pp. 581-585; 1990.

Bracco, D. et al., Bedside determination of fluid accumulation after cardiac surgery using segmental bioelectrical impedance, Critical Care Medicine, vol. 26, No. 6, pp. 1065-1070, 1998.

Chaudary, S.S. et al.; Dielectric Properties of Normal & Malignant Human Breast Tissues at Radiowave and Microwave Frequencies; Indian Journal of Biochemistry & Biophysics; vol. 21, No. 1, pp. 76-79; 1984.

Chiolero, R.L. et al.; Assessment of changes in body water by bioimpedance in acutely ill surgical patients; Intensive Care Medicine; vol. 18, pp. 322-326; 1992.

Chumlea et al.; Bioelectrical Impedance and Body Composition: Present Status and Future Directions; Nutrition Reviews; vol. 52, No. 4, pp. 123-131; 1994.

Cornish, B.H. et al.; Quantification of Lymphoedema using Multifrequency Bioimpedance; Applied Radiation and Isotopes; vol. 49, No. 5/6, pp. 651-652; 1998.

Cornish, B.H. et al.; Bioelectrical impedance for monitoring the efficacy of lymphoedema treatment programmes; Breast Cancer Research and Treatment; vol. 38, pp. 169-176; 1996.

Cornish, B.H. et al.; Data analysis in multiple-frequency bioelectrical impedance analysis; Physiological Measurement; vol. 19, No. 2, pp. 275-283; May 1, 1998.

Cornish, B.H. et al.; Alteration of the extracellular and total body water volumes measured by multiple frequency bioelectrical impedance analysis; Nutrition Research; vol. 14, No. 5, pp. 717-727; 1994.

Cornish, B.H. et al.; Early diagnosis of lymphedema using multiple frequency bioimpedance; Lymphology; vol. 34, pp. 2-11; Mar. 2001.

Cornish, B.H. et al.; Early diagnosis of lymphoedema in postsurgery breast cancer patients; Annals New York Academy of Sciences; pp. 571-575; May 2000.

De Luca, F. et al., Use of low-frequency electrical impedance measurements to determine phospoholipid content in amniotic fluid; Physics in Medicine and Biology, vol. 41, pp. 1863-1869, 1996.

Deurenberg, P. et al., Multi-frequency bioelectrical impedance: a comparison between the Cole-Cole modelling and Hanai equations with the classicaly impedance index approach, Annals of Human Biology, vol. 23, No. 1, pp. 31-40, 1996.

Dines K.A. et al.; Analysis of electrical conductivity imaging; Geophysics; vol. 46, No. 7, pp. 1025-1036; Jul. 1981.

Ellis, K.J. et al; Human hydrometry: comparison of multifrequency bioelectrical impedance with 2H2O and bromine dilution; Journal of Applied Physiology; vol. 85, No. 3, pp. 1056-1062; 1998.

Forslund, A.H. et al.; Evaluation of modified multicompartment models to calculate body composition in healthy males; American Journal of Clinical Nutrition; vol. 63, pp. 856-862; 1996.

Gersing, E.; Impedance spectroscopy on living tissue for determination of the state of Organs; Bioelectrochemistry and Bioenergetics; vol. 45, pp. 145-149; 1998.

Gerth, W.A. et al.; A computer-based bioelectrical impedance spectroscopic system for noninvasive assessment of compartmental fluid redistribution; Third Annual IEEE Symposium on Computer Based Medical Systems, Jun. 3-6, 1990, University of NC. at Chapel Hill; pp. 446-453; Jun. 1990.

Gudivaka R. et al; Single- and multifrequency models for bioelectrical impedance analysis of body water compartments; Applied Physiology; vol. 87, Issue 3, pp. 1087-1096; 1999.

Jones, C.H. et al; Extracellular fluid volume determined by bioelectric impedance and serum albumin in CAPD patients; Nephrology Dialysis Transplantation; vol. 13, pp. 393-397; 1998.

Jossinet, J. et al.; A Study for Breast Imaging with a Circular Array of Impedance Electrodes; Proc. Vth Int. Conf. Bioelectrical Impedance, 1981, Tokyo, Japan; pp. 83-86; 1981.

Jossinet, J. et al.; Technical Implementation and Evaluation of a Bioelectrical Breast Scanner; Proc. 10.sup.th Int. Conf. IEEE Engng. Med. Biol., 1988, New Orleans, USA (Imped. Imaging II); vol. 1. p. 289; 1988.

Kanai, H. et al.; Electrcial Measurment of Fluid Distribution in Legs and Arms; Medical Progress through technology; pp. 159-170; 1987.

Kim, C.T. et al.; Bioelectrical impedance changes in regional extracellular fluid alterations; Electromyography and Clinical Neurophysiology; vol. 37, pp. 297-304; 1997.

Lozano, A. et al.; Two-frequency impedance plethysmograph: real and imaginary parts; Medical & Biological Engineering & Computing; vol. 28, No. 1, pp. 38-42; Jan. 1990.

Liu R. et al; Primary Multi-frequency Data Analyze in Electrical Impedance Scanning; Proceedings of the IEEE-EMBS 2005, 27th Annual International Conference of the Engineering in Medicine and Biology Society, Shanghai, China; pp. 1504-1507; , Sep. 1-4, 2005.

Lukaski, H.C. et al.; Estimation of Body Fluid Volumes Using Tetrapolar Bioelectrical Impedance Measurements; Aviation, Space, and Environmental Medicine; pp. 1163-1169; Dec. 1998.

(56) References Cited

OTHER PUBLICATIONS

Man, B. et al. Results of Preclinical Tests for Breast Cancer Detection by Dielectric Measurements; XII Int. Conf. Med. Biol. Engng. 1979, Jerusalem, Israel. Springer Int., Berlin; Section 30.4; 1980.

Mattar, J.A., Application of Total Body Impedance to the Critically Ill Patient, New Horizons, vol. 4, No. 4, pp. 493-503, 1996.

McDougal D., et al.; Body Composition Measurements From Whole Body Resistance and Reactance; Surgical Forum; vol. 36, pp. 43-44; 1986.

Osterman K.S. et al.; Multifrequency electrical impedance imaging: preliminary in vivo experience in breast; Physiological Measurement; vol. 21, No. 1, pp. 99-109; Feb. 2000.

Ott, M. et al.; Bioelectrical Impedance Analysis as a Predictor of Survival in Patients with Human Immunodeficiency Virus Infection; Journal of Acquired Immune Deficiency Syndromes and Human Retrovirology; vol. 9, pp. 20-25; 1995.

Pethig, R. et al.; The Passive Electrical Properties of Biological Systems: Their Significance in Physiology, Biophysics and Biotechnology; Physics in Medicine and Biology; vol. 32, pp. 933-970; 1987.

Piperno, G. et al.; Breast Cancer Screening by Impedance Measurements; Frontiers of Medical & Biological Engineering; vol. 2, pp. 111-117; 1990.

Rigaud, B. et al.; Bioelectrical Impedance Techniques in Medicine; Critical Reviews in Biomedical Engineering; vol. 24 (4-6), pp. 257-351; 1996.

Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; vol. 5, pp. 1934-1935; Oct. 31, 1996.

Skidmore, R. et al.; A Data Collection System for Gathering Electrical Impedance Measurements from the Human Breast; Clinical Physics Physiological Measurement; vol. 8, pp. 99-102; 1987.

Sollish, B.D. et al.; Micropressor-assisted Screening Techniques; Israel Journal of Medical Sciences; vol. 17, pp. 859-864; 1981.

Steijaert, M. et al.; The use of multi-frequency impedance to determine total body water and extracellular water in obese and lean female individuals; International Journal of Obesity; vol. 21, pp. 930-934; 1997.

Surowiec, A.J. et al.; Dielectric Properties of Brest Carcinima and the Surrounding Tissues; IEEE Transactions on Biomedical Engineering; vol. 35, pp. 257-263; 1988.

Tedner, B.; Equipment Using Impedance Technique for Automatic Recording of Fluid-Volume Changes During Haemodialysis; Medical & Biological Engineering & Computing; pp. 285-290; 1983.

Thomas. B.J.; Future Technologies; Asia Pacific Journal Clinical Nutrition; vol. 4, pp. 157-159; 1995.

Thomas. B.J. et al.; Bioimpedance Spectrometry in Determination of Body Water Compartments: Accuracy and Clinical Significance; Applied Radiation and Isotopes; vol. 49, No. 5/6, pp. 447-455; 1998.

Thomas. B.J. et al.; Bioelectrical impedance analysis for measurement of body fluid volumes—A review; Journal of Clinical Engineering; vol. 17, No. 16, pp. 505-510; 1992.

Ulgen, Y. et al.; Electrical parameters of human blood; Engineering in Medicine and Biology Society, 1998. Proceedings of the 20th Annual International Conference of the IEEE; vol. 6, pp. 2983-2986; Nov. 1, 1998.

Ward, L.C. et al.; There is a better way to measure Lymphodema; National Lymphedema Network Newsletter; vol. 7, No. 4, pp. 89-92; Oct. 1995.

Ward, L.C. et al., Multi-frequency bioelectrical impedance augments the diagnosis and management of lymphoedema in post-mastectomy patients, European Journal of Clinical Investigation, vol. 22, pp. 751-754, 1992.

Woodrow, G. et al; Effects of icodextrin in automated peritoneal dialysis on blood pressure and bioelectrical impedance analysis; Nephrology Dialysis Transplantation; vol. 15, pp. 862-866; 2000.

Bella, et al., Relations Of Left Ventricular Mass To Fat-Free And Adipose Body Mass: The Strong Heart Study, (1998) Circulation, vol. 98, pp. 2538-2544.

Cornish, B.H, et al.; Optimizing Electrode Sites for Segmental Bioimpedance Measurements; Physiological Measurement; Institute of Physics; pp. 241-250, vol. 20, No. 3; 1999.

Cornish, B.H, et al.; A New Technique for the Quantification of Peripheral Edema with Application in Both Unilateral and Bilateral Cases; Angiology; pp. 41-47, vol. 53, No. 1; 2002.

Fenech, et al.; Extracellular and Intracellular vol. Variations During Postural Change Measured by Segmental and Wrist-Ankle Bioimpedance Spectroscopy; IEEE Transactions on Biomedical Engineering; IEEE Service Center; vol. 51, No. 1, pp. 166-175, 2004.

Golden, et al.; Assessment of Peripheral Hemodynmics using Impedance Plethysmogrphy; Physical Therapy; vol. 66, No. 10, pp. 1544-1547; 1986.

Iacobellis, G., et al. Influence Of Excess Fat On Cardiac Morphology And Function: Study In Uncomplicated Obesity, (2002) Obesity Research, vol. 10, pp. 767-773.

Ivorra, a., et al.; Bioimpedance dispersion width as a parameter to monitor living tissues; Physiol. Meas. 26 (2005) S165-S173.

Karason, K., et al., Impact Of Blood Pressure And Insulin On The Relationship Between Body Fat And Left Ventricular Structure, (2003) European Heart Journal, vol. 24, pp. 1500-1505.

Kim, et al.; Impedance Tomography and its Application in Deep Venous Thrombosis Detection; IEEE Engineering in Medicine and Biology Magazine; IEEE Service Center; vol. 8, No. 1, pp. 46-49; 1989.

McCullah, et al.; Bioelectrical Impedance Analysis Measures the Ejection Fraction of the Calf Muscle Pump; IFMBE Proceedings; vol. 17, pp. 616-619; 2007.

Nawarycz, et al.; Triple-frequency Electroimpedance Method for Evaluation of Body Water Compartments; Medical & Biological Engineering & Computing; vol. 34, No. Supp. 1, Pt. 2, pp. 181-182; 1996.

Noshiro, et al.; Electrical Impedance in the Lower Limbs of Patients with Duchenne Muscular Dystrophy: A Preliminary Study; Medical & Biological Engineering & Computing; vol. 31, No. 2, pp. 97-102; 1993.

Seo, et al.; Measuring Lower Leg Swelling: Optimum Frequency for Impedance Method; Medical & Biological Engineering & Computing; vol. 39, pp. 185-189; 2001.

Seoane, et al.; Current Source for Wideband Electrical Bioimpedance Spectroscopy Based on a Single Operational Amplifier; World Congress on Medical Physics and Biomedical Engineering; vol. 14, pp. 707-710; 2006.

Smith, et al.; A Pilot Study for Tissue Characterization Using Bioimpedance Mapping; 13th International Conference on Electrical Bio-impedance and the 8th Conference on Electrical Impedance Tomography; pp. 146-149; 2007.

Stanton, et al.; Non-invasive Assessment of the Lymphedematous Limb; Lymphology, The International Society of Lymphology; vol. 33, No. 3, pp. 122-135; 2000.

Ward, L.C. et al.; Determination of Cole parameters in multiple frequency bioelectrical impedance analysis using only the measurement of impedances; Four-frequency fitting; Physiological Measurement; vol. 27, No. 9, pp. 839-850; Sep. 2006.

Yoshinaga, M., Effect Of Total Adipose Weight And Systemic Hypertension On Left Ventricular Mass In Children, American Journal of Cardiology, (1995) vol. 76, pp. 785-787.

International Search Report from International Application No. PCT/AU2006/000924 dated Sep. 27, 2006.

International Search Report and Written Opinion of the International Searching Authority issued in PCT/AU2006/000922 dated Oct. 10, 2006.

International Search Report and Written Opinion of the International Searching Authority issued in PCT/AU2006/001057 dated Oct. 25, 2006.

(56) References Cited

OTHER PUBLICATIONS

International Search Report and Written Opinion of the International Searching Authority issued in PCT/AU2008/000034 dated Mar. 17, 2008.
International Search Report and Written Opinion of the International Searching Authority issued in PCT/AU2008/000588 dated Aug. 13, 2008.
International Search Report and Written Opinion of the International Searching Authority issued in PCT/AU2008/001521 dated Jan. 15, 2009.
International Search Report and Written Opinion of the International Searching Authority issued in PCT/AU2009/000163 dated Apr. 16, 2009.

* cited by examiner

OEDEMA DETECTION

RELATED APPLICATIONS

This application is a continuation of U.S. patent application Ser. No. 11/629,832, filed Mar. 25, 2008, which is a U.S. National Phase under 35 U.S. C. §371 of the International Patent Application No. PCT/AU05/00876, filed Jun. 17, 2005, which claims the benefit of Australian Patent Application No. 2004903314, filed Jun. 18, 2004. Each of these applications are incorporated by reference in their entirety.

BACKGROUND OF THE INVENTION

The present invention relates to a method and apparatus for detecting tissue oedema, and in particular, to a method and apparatus for detecting tissue oedema using impedance measurements.

DESCRIPTION OF THE PRIOR ART

The reference to any prior art in this specification is not, and should not be taken as, an acknowledgment or any form of suggestion that the prior art forms part of the common general knowledge.

Lymphoedema is a condition characterised by excess protein and oedema in the tissues as a result of reduced lymphatic transport capacity and/or reduced tissue proteolytic capacity in the presence of a normal lymphatic load. Acquired, or secondary lymphoedema, is caused by damaged or blocked lymphatic vessels. "The commonest inciting events are surgery and/or radiotherapy. However, onset of lymphoedema is unpredictable and may develop within days of its cause or at any time during a period of many years after that cause.

WO00/79255 describes a method of detection of oedema by measuring bioelectrical impedance at two different anatomical regions in the same subject at a single low frequency alternating current. The two measurements are analysed to obtain an indication of the presence of tissue oedema by comparing with data obtained from a normal population.

Other known methods of analysis of bioelectrical impedance measurements involve determining a phase and amplitude value for the measured signals. The measurement of amplitude is straightforward but the measurement of phase is more complicated and therefore the required equipment is costly.

SUMMARY OF THE PRESENT INVENTION

In a first broad form the present invention provides a method of detecting tissue oedema in a subject, the method including, in a processing system:
  a) determining a measured impedance for first and second body segments;
  b) for each body segment, and using the measured impedance, determining an index indicative of a ratio of the extra-cellular to intra-cellular fluid;
  c) determining an index ratio based on the index for the first and second body segments;
  d) determining the presence, absence or degree of tissue oedema based on the index ratio.

Typically the method includes, in the processing system:
  a) comparing the index ratio to at least one reference; and,
  b) determining the presence, absence or degree of tissue oedema based on the results of the comparison.

Typically the reference includes at least one of:
  a) a predetermined threshold;
  b) a tolerance determined from a normal population; and,
  c) a predetermined range.

Typically the reference includes an index ratio previously determined for the subject.

Typically the previously determined index ratio is determined prior to the subject undergoing at least one of:
  a) surgery; and,
  b) treatment.

Typically the first and second body segments are different types of body segment.

Typically the first and second body segments are limbs.

Typically the first body segment is a leg and the second body segment is an arm.

Typically the method includes, in the processing system:
  a) determining a plurality of measured impedances for each body segment, each measured impedance being measured at a corresponding measurement frequency; and,
  b) determining the index ratio based on the plurality of measured impedances.

Typically the method includes, in the processing system:
  a) determining values for parameters $R_0$ and $R_\infty$ from the measured impedance values; and,
  b) calculating the index (I) using the equation:

$$I = \frac{R_\infty}{R_0 - R_\infty}$$

where:
  $R_0$ is the resistance at zero frequency; and,
  $R_\infty$ is the resistance at infinite frequency.

Typically the method includes, in the processing system, determining the parameter values using the equation:

$$Z = R_\infty + \frac{R_0 - R_\infty}{1 + (j\omega\tau)^{(1-\alpha)}}$$

where:
  Z is the measured impedance at angular frequency $\omega$,
  $\tau$ is a time constant, and
  $\alpha$ has a value between 0 and 1; and Typically the method includes, in the processing system:
  a) determining the impedance of each body segment at four discrete frequencies; and,
  b) determining values for the parameters by solving the equation using four simultaneous equations.

Typically the method includes, in the processing system, determining the parameter values by:
  a) determining an impedance locus using the measured impedance values; and,
  b) using the impedance locus to determine the parameter values.

Typically the method includes, in the computer system, displaying an indication of at least one of:
  a) the parameter values;
  b) the ratio of extra-cellular to intra-cellular fluid; and,
  c) an indication of the at least one of the presence, absence or degree of tissue oedema in the subject.

In a second broad form the present invention provides apparatus for detecting tissue oedema in a subject, the apparatus including a processing system for:
  a) determining a measured impedance for first and second body segments;

b) for each body segment, and using the measured impedance, determining an index indicative of a ratio of the extra-cellular to intra-cellular fluid;
c) determining an index ratio based on the index for the first and second body segments;
d) determining the presence, absence or degree of tissue oedema based on the index ratio.

Typically the apparatus includes:
a) a current supply for generating an alternating current at each of a plurality of frequencies;
b) at least two supply electrodes for applying the generated alternating current to a subject;
c) at least two measurement electrodes for detecting a voltage across the subject; and,
d) a sensor coupled to the measurement electrodes for determining the voltage, the sensor being coupled to the processing system to thereby allow the processing system to determine the measured impedances.

Typically the apparatus is adapted to perform the method of the first broad form of the invention.

In a third broad form the present invention provides a method of diagnosing tissue oedema in a body region, the method including:
a) applying an alternating current signal at four or more discrete frequencies;
b) measuring an impedance at each frequency;
c) solving the equation:

$$Z = R_\infty + \frac{R_0 - R_\infty}{1 + (j\omega\tau)^{(1-\alpha)}}$$

to obtain parameters $R_0$, $R_\infty$, $\tau$ and $\alpha$,
where:
  $Z$ is the measured impedance at angular frequency $\omega$,
  $R_0$ is the resistance at zero frequency,
  $R_\infty$ is the resistance at infinite frequency,
  $\tau$ is a time constant, and
  $\alpha$ has a value between 0 and 1; and
d) using one or more of the parameters $R_0$, $R_\infty$, $\tau$ and $\alpha$ to diagnose tissue oedema in the body region.

Typically the method includes diagnosing tissue oedema by determining the presence, absence or degree of tissue oedema.

Typically the method includes:
a) determining the impedance at four discrete frequencies; and,
b) determining values for the parameters by solving the equation using four simultaneous equations.

Typically the method includes:
a) determining values of one or more of the parameters $R_0$, $R_\infty$, $\tau$ and $\alpha$ for first and second body regions;
b) comparing the results from the first body region with the results from the second body region to obtain an indication of the presence of tissue oedema.

Typically the method includes:
a) comparing the parameters $R_0$ and $R_\infty$ for each body region; and,
b) indicating tissue oedema if the difference is outside a tolerance determined from a normal population.

Typically the method includes:
a) calculating an index $R_i/R_e$ as indicative of the ratio of extracellular fluid to intracellular fluid;
  where
    $R_e$ is the resistance of extracellular fluid determined from $R_e = R_0$; and,
    $R_i$ is the resistance of intracellular fluid determined from $$R_i = \frac{R_\infty R_e}{R_e - R_\infty};$$

and
b) diagnosing tissue oedema in accordance with the determined index.

Typically the method includes indicating tissue oedema by displaying the indication as a position on a scale.

Typically the method is a method according to the first broad form of the invention.

In a fourth broad form the present invention provides apparatus for detecting tissue oedema, the apparatus including:
a) a current supply for applying an alternating current to an anatomical region at four or more discrete frequencies across a frequency range;
b) a monitor for monitoring the bioelectrical impedance of said region; and
c) a processing system for:
  i) analysing the bioelectrical impedance by solving:

$$Z = R_\infty + \frac{R_0 - R_\infty}{1 + (j\omega\tau)^{(1-\alpha)}}$$

to obtain parameters $R_0$, $R_\infty$, $\tau$ and $\alpha$,
where:
  $Z$ is the measured impedance at angular frequency $\omega$,
  $R_0$ is the resistance at zero frequency,
  $R_\infty$ is the resistance at infinite frequency,
  $\tau$ is a time constant, and
  $\alpha$ has a value between 0 and 1; and
  ii) using one or more of the parameters $R_0$, $R_\infty$, $\tau$ and $\alpha$ to provide an indication of tissue oedema.

Typically the current supply includes a proximal electrode and distal electrode in electrical connection with a power source.

Typically the monitor includes a first connection and second connection for location on or near the anatomical region.

Typically the monitor includes display means to display the signals indicative of bioimpedance.

Typically the processing system is suitably programmed to perform analysis of data to provide an indication of the presence of tissue oedema.

Typically the apparatus is adapted to perform the method of the third broad form of the invention.

In a fifth broad form the present invention provides a method of diagnosing tissue oedema in a body region, the method including:
a) calculating an index $R_i/R_e$ as indicative of the ratio of extracellular fluid to intracellular fluid;
  where:
    $R_e$ is the resistance of extracellular fluid determined from $R_e = R_0$; and,
    $R_i$ is the resistance of intracellular fluid determined from $$R_i = \frac{R_\infty R_e}{R_e - R_\infty};$$

and b) indicating the presence of tissue oedema if there is a change in the index $R_i/R_e$ over time.

Typically the method includes:
a) measuring of $R_i/R_e$ is made prior to an event likely to cause oedema; and,
b) comparing to a measurement of $R_i/R_e$ made after the event.

Typically the method is a method according to the first or third broad forms of the invention.

In a sixth broad form the present invention provides apparatus for diagnosing tissue oedema in a body region, the apparatus including a processing system for:
a) calculating an index $R_i/R_e$ as indicative of the ratio of extracellular fluid to intracellular fluid;
where:
$R_e$ is the resistance of extracellular fluid determined from $R_e=R_0$; and,
$R_i$ is the resistance of intracellular fluid determined from $$R_i = \frac{R_\infty R_e}{R_e - R_\infty};$$

and
b) indicating the presence of tissue oedema if there is a change in the index $R_i/R_e$ over time.

Typically the apparatus is adapted to perform the method of the fifth broad form of the invention.

BRIEF DESCRIPTION OF THE DRAWINGS

An example of the present invention will now be described with reference to the accompanying drawings, in which:—

DETAILED DESCRIPTION OF THE DRAWINGS

Figure 1:
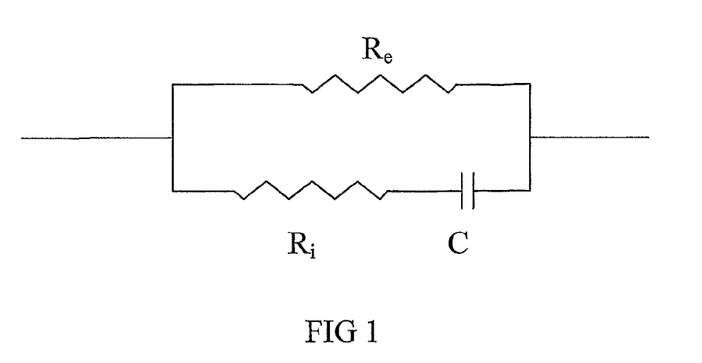
FIG. 1 is a schematic of an example of a theoretical equivalent circuit for biological tissue.

FIG. 1 is an example of an equivalent circuit that effectively models the electrical behaviour of biological tissue. The equivalent circuit has two branches that represent current flow through extracellular fluid and intracellular fluid. The extracellular component of biological impedance is represented by $R_e$ and the intracellular component is represented by $R_i$. Capacitance of the cell membrane in the intracellular path is represented by C.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals $R_e$. At infinite frequency the capacitor acts as a perfect conductor and the current passes through the parallel resistive combination. The resistance at infinite frequency is given by $R_\infty=R_iR_e/(R_i+R_e)$. The measured values of $R_0$ and $R_\infty$ would therefore directly provide the values of $R_e$ and $R_i$ required for estimation of extracellular water (ECW) and intracellular water (ICW), which lead to identification of oedema by comparison between affected and unaffected body regions. However, as is well known, the practical constraints of skin-electrode impedance do not permit application of DC or very high frequency AC currents, hence the values of the frequencies commonly used can only approximate the ideal measurement frequencies.

The impedance of the equivalent circuit of FIG. 1 at an angular frequency $\omega$, where $\omega=2\pi*$frequency, is given by:

$$Z = R_\infty + \frac{R_0 - R_\infty}{1 + (j\omega\tau)} \quad (1)$$

where:
$R_\infty=R_iR_e/(R_i+R_e)$,
$R_0=R_e$ and,
$\tau$ is the time constant of the capacitive circuit.

Figure 2:
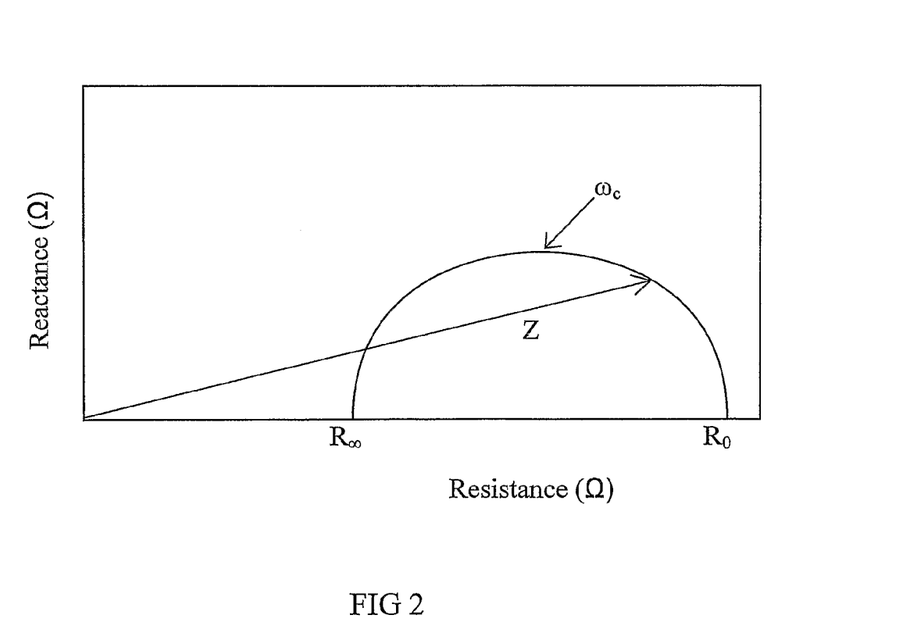
FIG. 2 is an example of a locus of impedance known as a Cole-Cole plot.

These values can be estimated by extrapolating what is known as a Cole-Cole plot, which is a plot of the vector sum of the resistance R and reactance X that sum to impedance Z. A Cole-Cole plot of reactance against resistance is shown in FIG. 2 with an impedance vector Z at a given frequency.

It is also known that biological specimens deviate from the equivalent circuit because the cell membrane is an imperfect capacitor and there is a large variation between cell types in the current path. This results in a Cole-Cole plot of a biological specimen having a depressed centre compared to the equivalent circuit plot shown in FIG. 2. A more accurate expression for impedance in a biological sample is therefore given by:

$$Z = R_\infty + \frac{R_0 - R_\infty}{1 + (j\omega\tau)^{(1-\alpha)}} \quad (2)$$

where $\alpha$ has a value between 0 and 1 and can be thought of as an indicator of the deviation of a real system from the ideal model.

Another important value is the impedance $Z_c$ at the peak of the locus in FIG. 2. This peak occurs when $\omega=1/\tau$, which is referred to as the characteristic angular frequency, $\omega_c$ which equals $2\pi f_c$.

As explained above, the prior art approach to determining the desired values of $R_0$ and $R_\infty$ has been to make impedance measurements at multiple frequencies and to construct a section of a Cole-Cole plot. The plot can be extrapolated to determine $R_0$, $R_\infty$ and $Z_c$. This procedure takes a significant amount of processing time and therefore makes real time monitoring of bioimpedance problematic. Furthermore, the measurements require determination of both phase and amplitude values which require relatively sophisticated, and therefore expensive, equipment.

Equation (2) has four, unknowns, $R_0$, $R_\infty$, $\tau$, and $\alpha$. The values of these unknowns can be determined by taking measurements at four discrete frequencies, and solving four simultaneous equations. Any of the established methods such as matrix inversion or numerical iteration can be used to solve the equations for the unknown values.

The values determined by this process compare favourably with the values obtained by the conventional curve fitting technique, in which measured impedances are used to plot a locus similar to that shown in FIG. 2, thereby allowing values of $R_0$ and $R_\infty$ to be obtained.

Greater, accuracy can be achieved by taking measurements at a larger number of frequencies, albeit at a cost in processing overhead. Furthermore, accurate results can usefully be derived by selecting discrete frequencies that span the range of frequencies normally used in multiple frequency bioelectrical impedance analysis (5 KHz to 1000 KHz).

Once the values of $R_0$, $R_\infty$, and $Z_c$ are determined they can be used in various ways to detect and quantify oedema in a body region. One approach to this quantification is to compare measurements taken at a first body region against measurements taken at a second body region.

The second measurements may be taken in a paired unaffected body region. For example, a first measurement may be made at a location on the left leg and a second measurement made at the same location on the right leg of the same patient where the right leg is unaffected by tissue oedema. It is clear to a skilled addressee that other paired anatomical regions may be similarly used when performing the above described methodology. For example, paired areas of the thorax may be assessed.

It is, however, possible to take the second measurement at a dissimilar body region. For example, the first reading may be taken on a leg, and a second reading may be taken on an arm. The analysis of these readings will necessarily involve some different considerations. Again, it is clear to a skilled addressee that a wide range of dissimilar anatomical structures may be used for these measurements, such as a leg and the chest wall. This form of the method is of particular use where two paired anatomical sites are both affected by tissue oedema. The comparison of readings taken in two such affected sites will be distorted and will not produce a reliable indicator of tissue oedema.

As a further alternative, the method may be applied to two or more measurements on the same anatomical region of a subject where those readings are separated in time. For example, a series of readings may be taken on a single limb prior to and subsequent to surgery with a known risk of lymphoedema as a side effect. Analysis of any two or more readings may indicate the early stage of developing lymphoedema and thereby provide a distinct advantage in that the prognosis may be greatly improved by early and aggressive therapeutic intervention. This technique may also be used to monitor the progress of oedema with comparison made between measurements of an affected site.

In the case of comparison of any two dissimilar regions it is known that a correcting factor may be required. A correcting factor may be established by surveying a population of clinically unaffected subjects:

Another approach is a modification of the technique described in a publication, (Cornish, B. H.; Thomas B. J.; Ward L. C.; Angiology Vol 53, No 1, pp 41-47 2002). In this approach the measured parameters are used to calculate an index Ri/Re. as indicative of the ratio of extracellular fluid to intracellular fluid. The extracellular fluid resistance Re is determined from $$R_e = R_0$$

and intracellular fluid resistance $R_i$ is determined from $$R_i = \frac{R_\infty R_e}{R_e - R_\infty}$$

Thus, the index I, which is indicative of the ratio of extra- to intra-cellular fluid is given by the equation:

$$I = \frac{R_i}{R_e} = \frac{R_\infty}{R_0 - R_\infty} \qquad (3)$$

This approach has particular application to monitoring oedema overtime as a plot of the index against time can disclose the onset and rate of advance of oedema.

Figure 3:
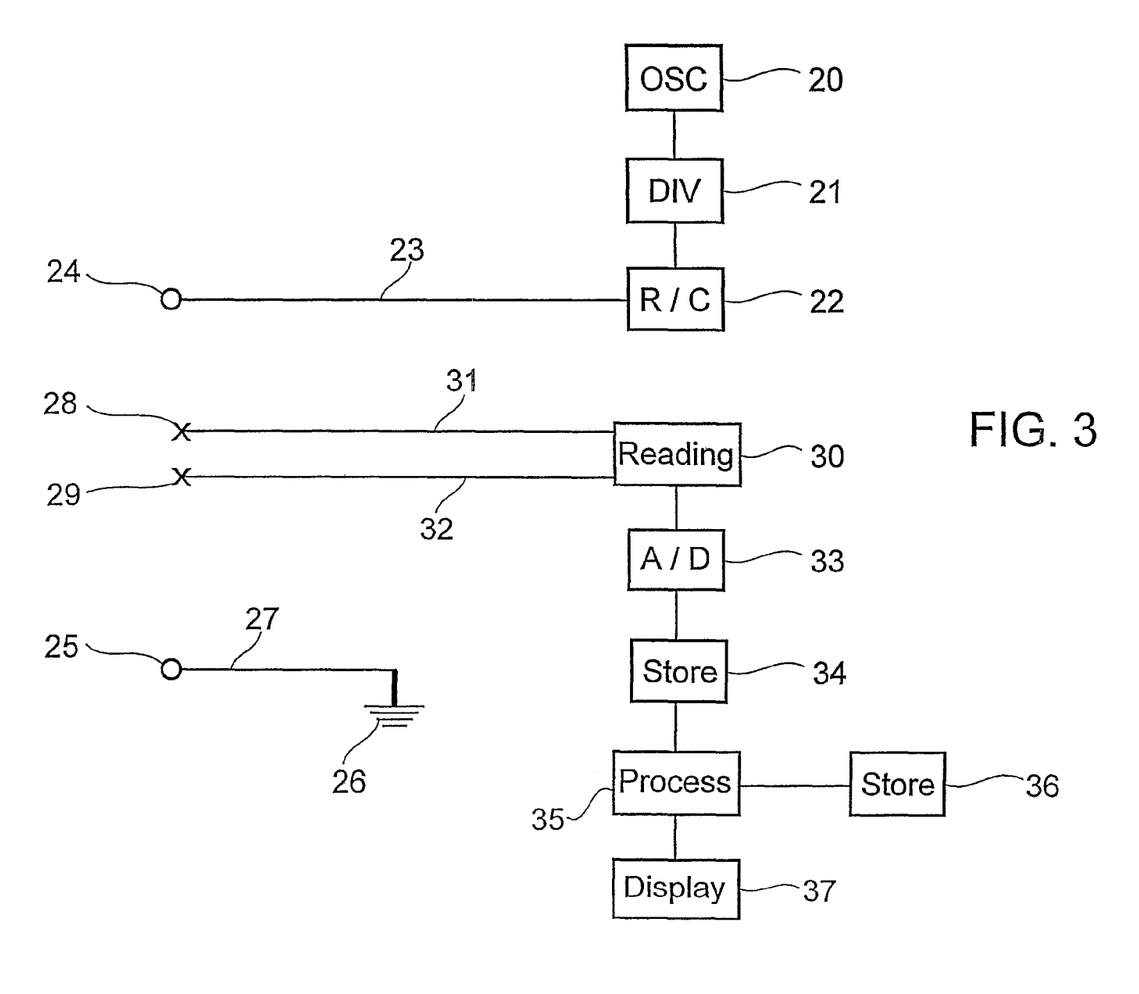
FIG. 3 is a schematic of an example of a single channel bioimpedance apparatus.

Referring to FIG. 3, there is shown a schematic of an apparatus for measuring impedance, including an oscillator 20, divider 21 and filter 22 connected in series to produce alternating current at a number of discrete frequencies when connected to a power, source (not shown). The alternating current passes through cable 23 to electrode 24 through intervening tissue (not shown) to electrode 25, which is connected to a reference 26 via cable 27.

Monitoring electrodes 28, 29 are in connection with bioimpedance measuring meter 30 via cables 31, 32. Signals from bioimpedance measuring meter 30 are passed to analogue/digital converter 33, which is in signal connection with data storing unit 34, which retains the digitised reading of bioimpedance.

The applied signal is suitably derived from a constant current source to ensure that the generated current does not exceed the Australian Standard of a maximum of 32V and a maximum current of 100 μA at 10 kHz. The current limit increases to an upper threshold of 1 mA at 1000 kHz. The applied signal could be derived from a constant voltage source rather than a constant current source providing a mechanism is provided to maintain the safety standard.

A first reading of bioelectrical impedance is taken from a first anatomical region of a subject and stored in data storing unit 34.

The processor 35 calculates the values $R_0$, $R_\infty$, $\tau$ and $\alpha$ by solving the equation (2) and transfers the result to second data storing unit 36. The values may also be presented on display 37.

The processor may also calculate an indicator of oedema, such as the $R_i/R_e$ index, and display this on a scale with a movable indicator. There may also be a simple series of lights which, when illuminated, indicate any one of "unaffected", "possibly affected" or "affected". The display may be any other suitable form of indicator.

Figure 4:
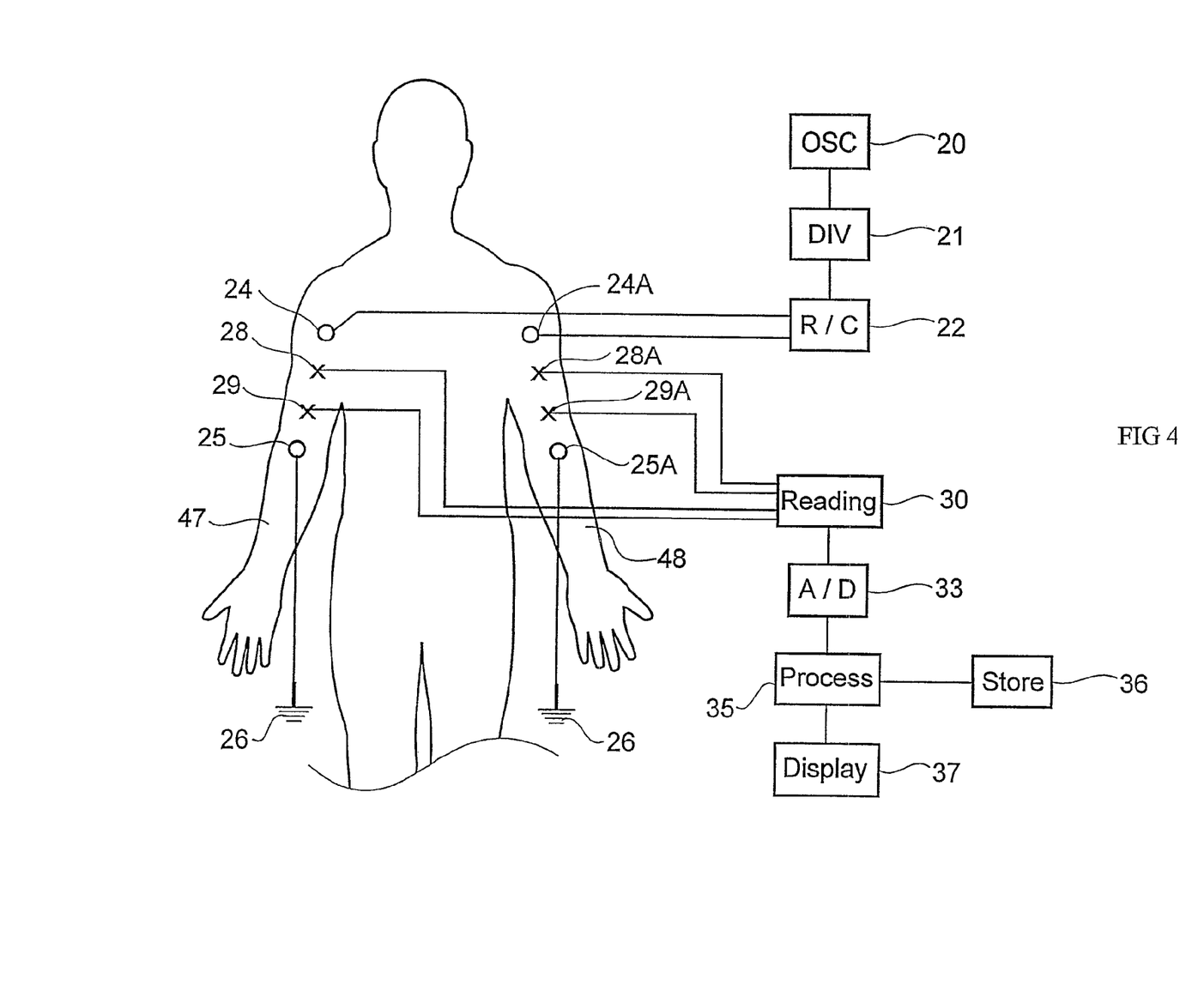
FIG. 4 is a schematic of an example of a dual channel bioimpedance apparatus; and, FIG. 5 is a flow chart of an example of a process for evaluating tissue oedema.

It is more convenient for many of the techniques for assessing oedema to use a two-channel bioimpedance meter as shown in FIG. 4. In this case, current is passed between the electrodes 24, 25 on, for example, one arm 47 and between the electrodes 24A, 25A on the opposite arm 48. This can be achieved either sequentially, for example through the use of multiplexing, or simultaneously. Monitoring electrodes 28, 29 on the first arm 47 measure bioelectrical impedance while monitoring electrodes 28A, 29A measure bioelectrical impedance on the opposite arm 48. A measuring meter 30 has two channels for simultaneously monitoring signals provided from the monitoring electrodes 28, 29; 28A; 29A. The signals are passed through an analogue/digital converter 33 and then analysed by processor 35. The results are stored in memory 36 and shown on display 37.

Accordingly the processor 35 operates to analyse the impedance signals and use this to provide an evaluation of the presence, absence or degree of tissue oedema. This is typically performed in accordance with applications software provided in the memory. It will be appreciated from this that the processor 35, the memory 36 and the display 37 may typically be formed from a processing system, such as a computer system, computer server, desktop computer, laptop, specialised hardware, or the like.

Figure 5:
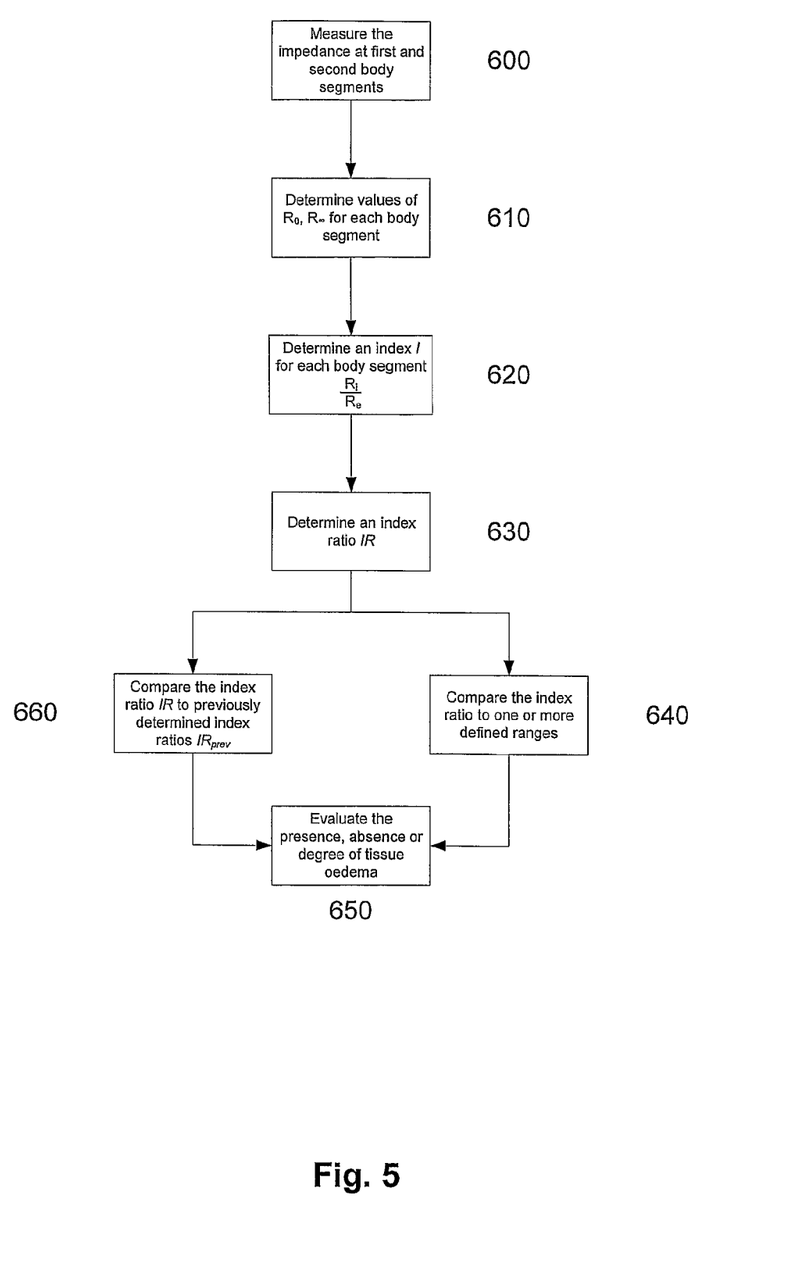

An example of the process for monitoring the impedance signals and evaluating tissue oedema will now be described with reference to the flowchart shown in FIG. 5.

In particular, at step 600, the impedance at first and second body segments are measured using the apparatus shown in FIG. 4. In this example, the body segments are different body segments and may include for example an arm and a leg.

At step 610 the processor 35 determines values of $R_0$ and $R_\infty$ for each body segment. This can be achieved using a number of mechanisms. For example, given that there are four unknown parameters $R_0$, $R_\infty$, $\tau$, $\alpha$, the equation (2) can be used to determine four simultaneous equations, which can then be solved using appropriate mathematical techniques. Alternatively, the measured impedance values can be plotted to derive an arc similar to that shown in FIG. 2, which then further allows the values of $R_0$ and $R_\infty$ to be determined. Alternative techniques may also be used.

At step 620 the values of $R_0$ and $R_\infty$ are used to determine an index I for each body segment. The index is based on the ratio of the extracellular to intracellular fluid and is therefore calculated using equation (3).

At step 630 an index ratio IR based on a ratio of the first body segment index $I_1$ to second body segment index $I_2$ is calculated, with this being used in evaluating the presence, absence or degree of oedema.

This is possible, as, for a healthy subject, there is generally a degree of similarity of intra- and extra-cellular fluid levels, even between different body segments. Thus, for example, if the subject is suffering from a condition other than oedema, which causes a general change in the ratio of extra- to intra-cellular fluid, then this should affect all body segments roughly equally. As a result, assuming that neither body segment has tissue oedema, then the index ratio IR should remain relatively constant for a given individual.

It will be appreciated that in the event that the properties of each body segment are equal, then the index ratio should have a value in the region of 1. Typically however, minor variations in tissue will occur between different body segments, and this can be accounted for in one of two ways.

Firstly, as shown at step 640, the index ratio IR can be compared to a predetermined range. In this case, the range is used to account for variations between body segments that are not attributable to tissue oedema. It will therefore be appreciated that the range is therefore typically set to take into account the difference in index ratio IR between different body portions in a number of different subjects. This range can therefore be set based on data collected from a number of healthy subjects.

In any event, if the index ratio IR falls outside the predetermined range, then this is used by the processor 35 to determine that tissue oedema is present in one of the body segments at step 650.

Furthermore, an assessment of the value of the index ratio IR can be used in assessing the degree of tissue oedema. Thus, for example, a number of value ranges can be defined, with each range corresponding to a different degree of oedema. In this instance, the processor 35 determines within which range the index ratio IR falls, and uses this to generate an indication of the likely degree of tissue oedema.

The value of the index ratio IR will also depend on the body segments that have been selected and accordingly, in general a different range will be selected for the comparison depending on the body segments under consideration.

It will also be appreciated that the index ratio IR can be used to indicate in which body segment the oedema is present, and this can be based on whether the index ratio IR is greater than or less than 1.

The index ratio IR may also depend on a number of factors, such as the subject's age, weight, sex and height, and again a respective range can be selected based on these factors. However, to avoid the need for an assessment of such factors, an alternative process of longitudinal analysis can be performed.

In this case, at step 660 the processor 35 can compare the index ratio IR to previously determined index ratios IR, measured for the same subject, on the same body segments. In this situation, the previously determined index ratios $IR_{prev}$ are preferably determined prior to the onset of oedema but this is not essential.

In any event, previous measurements of the same body segments on the same subject will automatically account for inherent variations in tissue properties, which in turn cause different values for the ratio of extra- to intra-cellular fluid even if tissue oedema is not present.

In this case, the processor 35 assesses whether the current index ratio JR value is different to the previous index ratio $IR_{prev}$. If there is change in the value, then the direction in change in value can indicate either increasing or decreasing levels of tissue oedema, with the magnitude of the change being used to indicate a degree of change at step 650.

In general, at step 650, the display 37 is used to display an indication of one or more of:
one or more index ratios
one or more indexes; and,
the presence, absence or degree of tissue oedema.

It will therefore be appreciated from this that the above-described methodology provides two different methods of determining the onset for oedema. This can be achieved either by performing a longitudinal analysis in which the index ratio R is compared to previously determined index ratios $IR_{prev}$. Alternatively the index ratio IR can be compared to one or more absolute index ratio ranges.

In practice, a combination for the two approaches will generally be used. Thus, for example, when a patient is first admitted for a procedure to be performed, a comparison to absolute index ratio ranges may be used to confirm that it is unlikely that the patient has oedema.

The measured index ratio IR can then be used to form the reference value of the index ratio $IR_{prev}$, allowing subsequent measurements to be compared thereto.

By using the index ratio IR described above, this allows variation in tissue properties between different body portions to be taken into account when assessing the presence, absence or degree of tissue oedema, and accordingly, this allows the onset of bilateral oedema to be detected. This is in contrast to previous techniques, in which like body segments are compared. In this case, if impedance measurements of a limb, such as a leg, are compared to measurements from the other corresponding limb, then in the event that oedema is present in both limbs, the impedance measurements will be similar, and will not therefore indicate that oedema is present.

As mentioned above, the values of $R_0$ and $R_\infty$ can be determined in any one of a number of ways. However, in general it is preferred to be able to determine the values in real-time to thereby vastly enhance the oedema assessment process. In particular, this allows measurements to be made of the patient, with the processor 35 generating an indication of the degree of tissue oedema in real-time.

The discussion has referred to both oedema and lymphoedema, as it is clear to a skilled addressee that the above method and apparatus may be utilised on any form of tissue oedema. However, it is also likely that the predominant use of the method, and apparatus will be directed mainly to lymphoedema due to its clinical relevance. However, this may change in a specific situation or with time. The method may also be used in comparing a reading from one anatomical region with a separate unpaired region. For example, a reading taken on central localised oedema (eg: ascites) may be referenced against a nonoedematous structure such as a limb.

Throughout the specification, the aim has been to describe the preferred embodiments of the invention without limiting the invention to any one embodiment or specific collection of features. Various changes and modifications may be made to the embodiments described and illustrated without departing from the present invention.

What is claimed is:

1. A method of diagnosing tissue oedema in a body region, the method including:
   calculating, using a processor of a processing system, an index $R_i/R_e$ as indicative of the ratio of extracellular fluid to intracellular fluid;
   where:
   $R_e$ is the resistance of extracellular fluid determined from $R_e=R_0$; and, $R_i$ is the resistance of intracellular fluid determined from $$R_i = \frac{R_\infty R_e}{R_e - R_\infty};$$

wherein:
   $R_\infty$ is the resistance of the body region at infinite applied frequency; and
   $R_0$ is the resistance of the body region at zero applied frequency; and
   displaying via the processing system an indicator indicating the presence of tissue oedema if there is a change in the index $R_i/R_e$ over time.

2. The method of claim 1, wherein the method includes:
   calculating of the index $R_i/R_e$ is made prior to an event likely to cause oedema; and,
   comparing to a measurement of the index $R_i/R_e$ made after the event.

3. The method of claim 1, additionally including, in the processing system:
   determining a measured impedance for first and second body segments;
   for each body segment, and using the measured impedance, determining the index $R_i/R_e$;
   determining an index ratio based on the index $R_i/R_e$ for the first and second body segments;
   determining the presence, absence or degree of tissue oedema based on the index ratio.

4. The method of claim 3, additionally including, in the processing system:
   comparing the index ratio to at least one reference; and
   determining the presence, absence or degree of tissue oedema based on the results of the comparison.

5. The method of claim 4, wherein the reference includes at least one of:
   a predetermined threshold;
   a tolerance determined from a normal population; and
   a predetermined range.

6. The method of claim 4, wherein the reference includes an index ratio previously determined for the subject.

7. The method of 6, wherein the previously determined index ratio is determined prior to the subject undergoing at least one of:
   surgery; and
   treatment.

8. The method of claim 4, wherein the first and second body segments are different types of body segment.

9. The method of claim 4, wherein the first and second body segments are limbs.

10. The method of claim 4, wherein the first body segment is a leg and the second body segment is an arm.

11. The method of claim 4, additionally including, in the processing system:
    determining a plurality of measured impedances for each body segment, each measured impedance being measured at a corresponding measurement frequency; and
    determining the index ratio based on the plurality of measured impedances.

12. The method of claim 1, additionally including, in the processing system, determining parameter values of parameters $R_0$ and $R_\infty$ using the equation:

$$Z = R_\infty + \frac{R_0 - R_\infty}{1 + (j\omega\tau)^{(1-\alpha)}}$$

where:
Z is the measured impedance at angular frequency $\omega$,
$\tau$ is a time constant, and
$\alpha$ has a value between 0 and 1.

13. The method of claim 12, wherein the method includes, in the processing system:
    determining the impedance of each body segment at four discrete frequencies; and
    determining values for the parameters by solving the equation using four simultaneous equations.

14. The method of claim 1, additionally including, in the processing system, determining parameter values of parameters $R_0$ and $R_\infty$ by:
    determining an impedance locus using the measured impedance values; and
    using the impedance locus to determine the parameter values.

15. The method of claim 1, additionally including, in the processing system, displaying an indication of at least one of:
    the parameter values of parameters $R_0$ and $R_\infty$;
    the ratio of extra-cellular to intra-cellular fluid; and
    an indication of the at least one of the presence, absence or degree of tissue oedema in the subject.

16. The method of claim 1, additionally including, in the processing system:
    applying an alternating current signal at four or more discrete frequencies;
    measuring an impedance at each frequency;
    solving the equation:

$$Z = R_\infty + \frac{R_0 - R_\infty}{1 + (j\omega\tau)^{(1-\alpha)}}$$

to obtain parameters $R_0$, $R_\infty$, $\tau$ and $\alpha$,
where:
Z is the measured impedance at angular frequency $\omega$,
$\tau$ is a time constant, and
$\alpha$ has a value between 0 and 1; and
using one or more of the parameters $R_0$, $R_\infty$, $\tau$ and $\alpha$ to diagnose tissue oedema in the body region.

17. The method of claim 16, additionally including diagnosing tissue oedema by determining the presence, absence or degree of tissue oedema.

18. The method of claim 16, additionally including, in the processing system:
  determining the impedance at four discrete frequencies; and
  determining values for the parameters by solving the equation using four simultaneous equations.

19. The method of claim 16, additionally including, in the processing system:
  determining values of one or more of the parameters $R_0$, $R_\infty$, $\tau$ and $\alpha$ for first and second body regions;
  comparing the results from the first body region with the results from the second body region to obtain an indication of the presence of tissue oedema.

20. The method of claim 19, additionally including, in the processing system:
  comparing the parameters $R_0$ and $R_\infty$ for each body region; and,
  indicating tissue oedema if the difference is outside a tolerance determined from a normal population.

21. The method of claim 16, additionally including, in the processing system, indicating tissue oedema by displaying the indication as a position on a scale.

22. An apparatus for diagnosing tissue oedema in a body region, the apparatus including a processing system configured to:
  calculate, using a processor of the processing system, an index $R_i/R_e$ as indicative of the ratio of extracellular fluid to intracellular fluid;
  where:
    $R_e$ is the resistance of extracellular fluid determined from $R_e = R_0$;
    $R_i$ is the resistance of intracellular fluid determined from $$R_i = \frac{R_\infty R_e}{R_e - R_\infty};$$

and
    $R_\infty$ is the resistance of the body region at infinite applied frequency; and
    $R_0$ is the resistance of the body region at zero applied frequency; and
  display via the processing system an indicator indicating the presence of tissue oedema if there is a change in the index $R_i/R_e$ over time.

23. The apparatus of claim 22, wherein measuring of the index $R_i/R_e$ is made prior to an event likely to cause oedema, and the processing system is configured to compare to a measurement of the index $R_i/R_e$ made after the event.

24. The apparatus of claim 22, wherein the processing system is configured to:
  determine a measured impedance for first and second body segments;
  for each body segment, and using the measured impedance, determine the index $R_i/R_e$;
  determine an index ratio based on the index $R_i/R_e$ for the first and second body segments; and
  determine the presence, absence or degree of tissue oedema based on the index ratio.

25. The apparatus of claim 24, wherein the processing system is configured to:
  compare the index ratio to at least one reference; and
  determine the presence, absence or degree of tissue oedema based on the results of the comparison.

26. The apparatus of claim 25, wherein the reference includes at least one of:
  a predetermined threshold;
  a tolerance determined from a normal population; and
  a predetermined range.

27. The apparatus of claim 25, wherein the reference includes an index ratio previously determined for the subject.

28. The apparatus of claim 27, wherein the previously determined index ratio is determined prior to the subject undergoing at least one of:
  surgery; and
  treatment.

29. The apparatus of claim 25, wherein the first and second body segments are different types of body segment.

30. The apparatus of claim 25, wherein the first and second body segments are limbs.

31. The apparatus of claim 25, wherein the first body segment is a leg and the second body segment is an arm.

32. The apparatus of claim 25, wherein the processing system is configured to:
  determine a plurality of measured impedances for each body segment, each measured impedance being measured at a corresponding measurement frequency; and,
  determine the index ratio based on the plurality of measured impedances.

33. The apparatus of claim 22, wherein the processing system is configured to determine parameter values of parameters $R_0$ and $R_\infty$ using the equation:

$$Z = R_\infty + \frac{R_0 - R_\infty}{1 + (j\omega\tau)^{(1-\alpha)}}$$

where:
  Z is the measured impedance at angular frequency $\omega$,
  $\tau$ is a time constant, and
  $\alpha$ has a value between 0 and 1.

34. The apparatus of claim 33, wherein the processing system is configured to:
  determine the impedance of each body segment at four discrete frequencies; and
  determine values for the parameters by solving the equation using four simultaneous equations.

35. The apparatus of claim 22, wherein the processing system is configured to determine parameter values of parameters $R_0$ and $R_\infty$ by:
  determining an impedance locus using the measured impedance values; and
  using the impedance locus to determine the parameter values.

36. The apparatus of claim 22, wherein the processing system is configured to display an indication of at least one of:
  the parameter values of parameters $R_0$ and $R_\infty$;
  the ratio of extra-cellular to intra-cellular fluid; and,
  an indication of the at least one of the presence, absence or degree of tissue oedema in the subject.

37. The apparatus of claim 22, wherein the processing system is configured to:
  apply an alternating current signal at four or more discrete frequencies;
  measure an impedance at each frequency;
  solve the equation:

$$Z = R_\infty + \frac{R_0 - R_\infty}{1 + (j\omega\tau)^{(1-\alpha)}}$$

to obtain parameters $R_0$, $R_\infty$, $\tau$ and $\alpha$, where:
- $Z$ is the measured impedance at angular frequency $\omega$,
- $\tau$ is a time constant, and
- $\alpha$ has a value between 0 and 1; and use one or more of the parameters $R_0$, $R_\infty$, $\tau$ and $\alpha$ to diagnose tissue oedema in the body region.

38. The apparatus of claim 37, wherein the processing system is configured to diagnose tissue oedema by determining the presence, absence or degree of tissue oedema.

39. The apparatus of claim 37, wherein the processing system is configured to:
determine the impedance at four discrete frequencies; and
determine values for the parameters by solving the equation using four simultaneous equations.

40. The apparatus of claims 37, wherein the processing system is configured to:
determine values of one or more of the parameters $R_0$, $R_\infty$, $\tau$ and $\alpha$ for first and second body regions; and
compare the results from the first body region with the results from the second body region to obtain an indication of the presence of tissue oedema.

41. The apparatus of claim 40, wherein the processing system is configured to:
compare the parameters $R_o$ and $R_\infty$ for each body region; and
indicate tissue oedema if the difference is outside a tolerance determined from a normal population.

42. The apparatus of claim 27, wherein the processing system is configured to indicate tissue oedema by displaying the indication as a position on a scale.

43. The apparatus of claim 22, wherein the apparatus includes:
a current supply for generating an alternating current at each of a plurality of frequencies;
at least two supply electrodes for applying the generated alternating current to the body region;
at least two measurement electrodes for detecting a voltage across the body region; and,
a sensor coupled to the measurement electrodes for determining the voltage, the sensor being coupled to the processing system to thereby allow the processing system to determine the measured impedances.

44. The apparatus of claim 43, wherein the current supply generates an alternating current at four or more discrete frequencies across a frequency range.

45. The apparatus of claim 22, wherein the apparatus includes a two-channel bioimpedance meter.

46. The apparatus of claim 45, wherein current is passed between supply electrodes on first and second body segments and a voltage is sensed between measurement electrodes on the first and second body segments.

47. The apparatus of claim 22, wherein the apparatus displays an indication of whether the body region is "unaffected", "possibly affected" or "affected".

48. The method of claim 1, wherein the indicator indicates if the body region is "unaffected", "possibly affected" or "affected".

49. The method of claim 1, wherein the method is performed on a body region at risk of oedema.

50. The method of claim 1, additionally including:
applying an alternating current at four or more discrete frequencies via a first pair of electrodes;
measuring an impedance at each of the four or more discrete frequencies via a second pair of electrodes; and
using the measured impedance in diagnosing tissue odema in the body region.

51. A bioimpedance apparatus for detecting the presence of oedema, the bioimpedance apparatus including:
a processing system configured to calculate an index $R_i/R_e$ indicative of the ratio of extracellular fluid to intracellular fluid, where:
$R_\infty$ is the resistance of the body region at infinite applied frequency
$R_0$ is the resistance of the body region at zero applied frequency
$R_e$ is the resistance of extracellular fluid determined from $R_e = R_0$; and
$R_i$ is the resistance of intracellular fluid determined from $$R_i = \frac{R_\infty R_e}{R_e - R_\infty};$$

and
a display configured to display an indicator indicative of the presence of odema if there is a change in the index $R_i/R_e$ over time.

52. The bioimpedance apparatus of claim 51, wherein the apparatus includes:
a current supply for generating an alternating current at each of a plurality of frequencies;
at least two supply electrodes for applying the generated alternating current to the body region;
at least two measurement electrodes for detecting a voltage across the body region; and,
a sensor coupled to the measurement electrodes for determining the voltage, the sensor being coupled to the processing system to thereby allow the processing system to determine the measured impedances.

* * * * *